United States Patent [19]

Grundy et al.

[11] Patent Number: 5,883,225
[45] Date of Patent: Mar. 16, 1999

[54] RELATING TO THE DETECTION OF VIRUSES

[75] Inventors: Jane Grundy; Vincent Emery; Paul Griffiths, all of London, England

[73] Assignee: Royal Free Hospital School of Medicine, London, England

[21] Appl. No.: 468,042

[22] Filed: Jun. 6, 1995

Related U.S. Application Data

[62] Division of Ser. No. 197,811, Feb. 17, 1994, Pat. No. 5,567,582, which is a continuation of Ser. No. 946,472, filed as PCT/GB91/00574 Apr. 11, 1991, abandoned.

[30] Foreign Application Priority Data

Apr. 11, 1990 [GB] United Kingdom .................. 9008223

[51] Int. Cl.[6] .................................................. C07K 14/045
[52] U.S. Cl. .......................... 530/350; 530/300; 530/826; 530/395
[58] Field of Search ...................................... 530/395, 300, 530/826, 350, 387.1, 389.4; 424/130.1

[56] References Cited

U.S. PATENT DOCUMENTS 5,547,834  8/1996  Spaete et al. ............................... 435/5

OTHER PUBLICATIONS

Cranage et al., The EMBO Journal 5(11):3057–3063 (1986).

*Primary Examiner*—Stephanie W. Zitomer
*Attorney, Agent, or Firm*—Nixon & Vanderhye P.C.

[57] ABSTRACT

The present invention relates to polypeptides from clinical isolates of cytomegalovirus encoded by the gB coding region which include at least one amino acid variation which is a substitution, insertion or deletion wherein the polypeptides otherwise retain the character of cytomegalovirus. The amino acid variations include changes to neutralizing epitopes.

12 Claims, 1 Drawing Sheet

Fig.1.

HIND III RESTRICTION MAPS OF STRAINS AD169 (A), DAVIS (D), AND TOWNE (T) AND 28 CLINICAL ISOLATES OF HUMAN CYTOMEGALOVIRUS.

RELATING TO THE DETECTION OF VIRUSES

This is a divisional of application Ser. No. 08/197,811, filed Feb. 17, 1994, now U.S. Pat. 5,567,582, which is a continuation of application Ser. No. 07/946,472, filed Nov. 10, 1992, the National Stage application of PCT/GB91/00574, filed Apr. 11, 1991, now abandoned, which claims priority to GB 9008223.1, filed Apr. 11, 1990.

This invention relates to the detection of viruses or virus antibodies and is particularly concerned with the detection of viruses of the Herpes group, the production and detection of antibodies to such viruses, and to vaccines against these viruses.

The Herpes group of viruses are a group of considerable clinical significance, the most important members of the group being Herpes Simplex (HSV), Cytomegalovirus (CMV), Epstein Barr virus (EBV) and Varicella-zoster virus (VZV). Infections with CMV occur frequently in the United Kingdom so that 60% of adults have evidence of past infection. Occasionally, the virus produces cases of Paul Bunnell negative glandular fever but the vast majority of infected people remain entirely asymptomatic. This virus infection is therefore primarily of medical importance in specific groups of patients which are neonates with congenital infection, and immuno-compromised individuals, such as recipients of renal or bone marrow allografts or patients with the acquired immunodeficiency syndrome (AIDS). In each of these groups of patients, CMV is an important pathogen and it would be very desirable, from the clinical point of view, to have available an assay method that can reliably identify the presence CMV in clinical samples.

The DNA sequence of the entire CMV genome has now been determined (Chee et al, 1989). The virus has 54 reading frames characteristic of glycoprotein genes or exons of glycoprotein genes. It is not however known how many of these potential glycoproteins are actually translated in the infected cell, expressed on the infective cell surface, or actually incorporated into the virus particle. Two CKV glycoproteins, named gB (Cranage et al 1986) and gH (Cranage et al 1988), have been well studied, and have been shown to be present on the viral envelope. They have both been shown to be recognised by neutralising murine monoclonal antibodies (Utz et al 1989, Rasmussen et al 1984), suggesting that these proteins are important for the infectivity of the virus and are thus potential candidates for a subunit CMV vaccine.

The majority of neutralising murine monoclonal antibodies raised against CMV recognise gB rather than gH (Gompels et al 1988), suggesting that in the mouse at least gB is more immunogenic than gH. The neutralising epitope recognised by one gB-specific antibody, 7–17, which neutralises CMV in vitro has recently been determined (Utz et al 1989). Using overlapping fragments of the open reading frame for gB from the laboratory strain AD169 expressed as β-galactosidase fusion proteins in *E. coli*, the antibody was shown to recognise a linear sequence between amino acid residues 609 and 626. Liu et al (1989) used overlapping synthetic hexapeptides from the gB sequence of the Towne laboratory strain and identified two other linear neutralising epitopes, mapping to residues 559–567 and 589–594. Banks et al (1989), using the Towne strain of CMV, identified at least two epitopes of gB which may be neutralised by murine monoclonal antibodies. These two epitopes occur between residues 620–680. Therefore, in addition to the two sites described by Liu et al and the one described by Utz et al, there is at least one further neutralising epitope recognised by murine monoclonal antibodies to the gB molecule.

Sequence SEQ ID NO:1 shows the DNA and peptide sequence of a region of the laboratory strain AD169. This region is part of the gB gene. The numbering to the DNA follows conventional usage, e.g. as described in EP-A-236 145. SEQ ID NO:2 shows the translation of the open reading frame of SEQ ID NO:1. The numbering follows the same usage as SEQ ID NO:1.

FIG. 1 shows an analysis of Hind III digests of CMV DNA from 3 laboratory samples and 28 clinical isolates of CMV.

The epitopes of the gB molecule described above are of particular importance in the laboratory for both biological studies and clinical purposes. Antibodies to these epitopes, such as the antibody 7–17, are of use as diagnostic agents. In addition, because CMV can establish latency and is also potentially oncogenic, ethical considerations preclude the use of a live attenuated CMV vaccine. Therefore, potential CMV vaccines will probably be based on important viral proteins rather than attenuated virus.

A vaccine against CMV based on one or more epitopes of gB will only be effective against wild-type strains of CMV encountered in clinical practice if the corresponding epitopes of the laboratory strains upon which the vaccines are based correspond to the clinical strains. Similarly, antibodies raised against laboratory strains will only detect clinical isolates of CMV which include epitopes closely similar, if not identical, to those against which the antibodies were raised. Clearly, differences between laboratory and clinical strains could result in vaccines against CMV which are ineffective, or diagnostic antibodies which give false negatives.

We have now isolated and analyzed clinical CMV samples by restriction enzyme digestion with Hind III. FIG. 1 shows such an analysis for 28 CMV strains found in the clinic (1–28) and a comparison with 3 tissue culture strains, AD169(A) Towne(T) and Davis(D). Although each isolate has a unique Hind III restriction profile, each profile contains polymorphisms which appear to segregate with aspects of the three laboratory adapted strains. For example, fragment J a of AD169 contains an additional Hind III site in the Towne and Davis and strains and this feature is also shared by clinical samples 9–12 and 28. In all, some specific polymorphisms may occur more frequently within the wild type population implying that only certain strains of virus are replication competent and that these are the species observed following culture of clinical specimens.

Global restriction analysis of the type described above does not however provide any information on the functional significance of sequence heterogeneities. There may also be sequence heterogenerities within large scale polymorphic fragments which will not be identified by this analysis. Thus, although restriction enzyme analysis of the gB region may indicate similarity between laboratory and clinical strains, no information concerning specific sequence variation can be deduced. For instance, it can not be determined whether the variation in restriction sites occurs in important epitopes or outside such regions.

We have now surprisingly found that there is DNA sequence variation, some of which results in amino acid variation, in the gB coding region of clinical isolates of CMV. This includes sequence variation in the epitope recognised by the antibody 7–17.

Although CKV may be analyzed by any suitable means known in the art, the size of the CMV virus, at 235 kb being the largest viral genome known to infect man, precludes some techniques from being of use when the variation in a large number of samples is to be analyzed. We have used the polymerase chain reaction (PCR; Saiki et al 1988) to amplify a 100 nucleotide fragment from the gB gene that encompasses a neutralising epitope of interest of each clinical CMV isolate. The amplified DNA is then cloned into suitable plasmid vectors and the DNA sequence of at least 3 individual clones of each isolate determined. The particular results obtained are presented in the examples which follows.

Although many of the DNA substitutions identified result in no change to the amino acid sequence, certain changes do result in alterations to the previously determined amino acid sequence of gB. In particular, amino acid residue number 612, leucine, has been identified as a residue which may be substituted. More specifically, this residue may be replaced by His, Val or Phe. Residue number 622, asparagine, may also be substituted. In particular, it may be replaced by tyrosine. Residue number 645, aspartic acid may also be substituted. In particular, it may be replaced by glycine.

Changes to the amino acid sequence of neutralising epitopes are especially significant, since this may result in the failure of an antibody to the unaltered epitope to recognise the changed epitope. Likewise, if a clinical sample is being analyzed for the presence of antibodies to an epitope of CMV via the use of peptides comprising an unaltered peptide sequence, such antibodies may not be detected if they have been produced against an altered epitope.

In the clinical situation, this may result in false negatives when samples are being analyzed for the presence of CMV. The present invention thus provides:

DNA of the SEQ ID NO:1 which includes at least one variation, for example 1, 2, 3 or 4 to 10 variations, which is a substitution, insertion or deletion, but which otherwise retains the character of CMV, and fragments thereof;

preferred variation being one or more, for example 2, 3, or 4 to 10, substitutions, at least one of which results in the alteration of the translation of the DNA;

particularly preferred DNA fragments of the type described above being those corresponding to nucleotides 1831–1857, 1921–1938, 1981–2034, 2068–2115 and fragments thereof;

recombinant vectors, eg plasmids, phage or virus, carrying such DNAs, and optionally containing sequences for the selection of the said vectors and/or signals for the expression of the DNA; and cells, eg bacterial, yeast, insect or mammalian, transfected or transformed with the above vectors.

The DNA sequences of the invention will preferably be at least 80%, eg 90, 95 or 99% homologous to a region of corresponding length of the SEQ ID NO:1.

Particular substitutions which are preferred are shown in Table 1 as sequences 1–27.

The DNA SEQ ID NO:1 and where appropriate fragments thereof, consisting of the following substitutions found in the Towne strain of DCV:

1854 C to T,
1897 C to A,
1947 C to T,
2019 G to C,
2076 T to C,
2106 G to A,
2109 T to C,
2127 T to C,
2166 G to A,
2167 C to T,
2190 C to T and
2196 A To G is excluded from the invention.

The invention also provides polypeptides of the sequence of SEQ ID NO:2 which include at least one variation for example 1, 2, 3 or 4 to 10 variations which is a substitution, insertion or deletion, but which otherwise retains the character of CMV. Peptides of this type corresponding to residues 559–567, 589–594, 609–626, 638–653 and fragments thereof are preferred, and the peptide 609–626 and fragments thereof is especially preferred.

Of the peptides of the invention which correspond to residues 609–626 and fragments thereof, those with substitutions at residues 612 or 622 (when they are present) are particularly preferred. More precisely, the following substitutions are especially preferred:

612 Leu-His
612 Leu-Val
612 Leu-Phe
622 Asn-Tyr
645 Asp-Gly.

The substitution at 622 may occur alone or in combination with each other or with any of the substitutions at 612, e.g., 612 Leu-His.

The peptide sequences of the invention will preferably be at least 80%, e.g. 85% or 90% homologous to a region of corresponding length of SEQ ID NO:2.

The peptides may be produced by synthetic means known in the art of peptide chemistry or by recombinant means, e.g., using an expression vector of the type described hereinbefore.

The term "retains the character of CMV", means that when a DNA (or peptide) sequence of the invention is included in a gB gene (or protein) which in turn forms part of a CMV genome, the CMV genome will be capable of reproduction in a host system in a manner substantially similar to wild-type CMV strains. Thus a CMV virus which comprises a DNA (or peptide) sequence of the present invention will be able to produce proteins essential for its reproduction in a host cell, and also produce other proteins capable of associating with each other for the formation of virus particles.

The invention further provides antibodies to the peptides of the invention. The antibodies may be polyclonal or monoclonal.

Polyclonal antibodies may be produced by conventional means, e.g., injecting a host animal e.g., a rat or rabbit with a peptide of the invention, optionally linked to a carrier, and recovering immune serum.

Monoclonal antibodies may also be produced by conventional methods, e.g., following the above procedure for the preparation of polyclonal antibodies but sacrificing the host animal and fusing its spleen cells with an immortalizing cell line, e.g., a mouse myeloma cell line.

Antibodies according to the invention may be whole antibodies or binding fragments thereof, i.e. fragments which retain the ability to bind to antigen to which it was raised. Antibodies also include altered antibodies, e.g., humanized antibodies as described in EP-A-0125023 (Genentech), or chimeric antibodies as described in EP-A-0239400 (Winter).

The invention further provides a kit for the detection of the presence of a CMV virus strain or antibodies against the strain in a sample, eg the serum of a patient, which comprises a peptide of the invention or an antibody thereto of the type described above, the said peptide or antibody being optionally immobilized and/or labelled, eg with an enzyme, fluorescent marker or radiolabel.

The CMV virus may be detected in a sample by using the above peptides as a binding agent to look for the presence or absence of antibodies, or by using antibodies of the invention as described above to look for the presence or absence of CMV viral proteins.

The invention further provides a vaccine for the treatment or prophylaxis of CMV virus infections which comprises a peptide or an antibody of the type described above in association with a pharmaceutically acceptable carrier or diluent. A peptide vaccine may be administered as free peptide, peptide attached to a carrier molecule, or form part of a recombinant epitope of a clinically acceptable carrier virus, e.g. vaccinia virus.

The following example illustrates the invention.

EXAMPLE 1

Patients undergoing renal or bone marrow transplantation at the Royal Free Hospital have surveillance cultures of urine, saliva and blood collected weekly. Clinical specimens were tested for the presence of CMV and were simultaneously inoculated onto primary Human embryo lung fibroblasts for CMV culture.

Clinical isolates of HCMV were propagated for 1–2 passages in primary human embryo lung fibroblasts. Viral DNA was isolated as follows: after discarding culture supernatants, Lysis buffer (0.1M Tris -HCl pH 7.5, 0.001M EDTA, 0.5% SDS) was added to the cells and chromosomal DNA was removed from the lysates by overnight precipitation with NaCl (5M; 0.25 volumes) at 4° C. Following centrifugation at 20,000 g for 30 minutes at 4° C., supernatants containing viral DNA were collected. Viral DNA was purified by treatment with proteinase K (200 µg/ml) followed by phenol/chloroform extraction and finally precipitation with ethanol.

DNA derived from each clinical isolate of HCMV was digested with Hind III and the resulting DNA fragments resolved by electrophoresis through a 0.7% agarose gel. DNA fragments were transferred to nylon filters (Hybond N, Amersham International) and probed using $^{32}$p labelled cloned Hind III restriction fragments derived from the unique long and unique short regions of the HCMV AD169 genome using a random priming kit (Amersham International) and established methodologies (Sambrook et al, 1989).

PCR amplification was performed essentially as described by Saiki and coworkers (1986). The primers used for the PCR amplification were as follows:

Primer 1: 5'-GAGGACAACGAAATCCTGTTGGGCA (SEQ ID NO:3)
Primer 2: 5'-GTCGACGGTGGAGATACTGCTGAGG (SEQ ID NO:4)

The reaction mixture contained the following components: CMV DNA (100 ng), 25 mM Tris-HCl pH 8.9, 17 mM ammonium sulphate, 3 mM magnesium chloride, 10 mM 2-mercaptoethanol, 0.002% gelatin, 1 µM of 5'-phosphorylated (Sambrook et al, 1990) HCMV specific primers, 200 µM of each of the deoxynucleotides (dATP, dCTP, dGTP, dTTP and 1 unit of Taq polymerase (Amplitaq, Perkin Elmer-Cetus) in a total volume of 100 ul. The reaction mixture was overlaid with 100 ul of mineral oil and the samples denatured by heating to 95° C. for 6 minutes and then amplified by 35 PCR cycles using a Hybaid thermal reactor (HBTR1). One cycle involved denaturation at 94° C. for 90 seconds, primer annealing at 60° C. for 90 seconds and extension at 72° C. for 120 seconds. After the final cycle the samples were incubated at 72° C. for a further 10 minutes.

Amplified products (100 base pairs) were analysed on a 1.6% agarose gel containing ethidium bromide and their authenticity confirmed by Souther blotting and hybridisation with a $^{32}$P-labelled AD169 Hind III F probe.

The 100 base pair PCR amplified products were treated with the Klenow fragment of DNA polymerase I (Amersham) in the presence of deoxynucleotide triphosphates (2.5 mM) to create blunt ended fragments then 5' phosphorylated with polynucleotide kinase and ATP as described by Sambrook et al (1989). The resulting fragments were ligated into Sma I cut dephosphorylated pT7T3/18U (Pharmacia). Following transformation of competent *E.coli* JM 109, clones containing the fragment were identified by colony hybridisation using a $^{32}$P-labelled AD169 Hind III F probe (Sambrook et al, 1989).

The clones were sequenced on both strands according to the plasmid sequencing protocols developed by Chen and Seeburg (1985). At least three clones were sequenced on both strands for PCR products derived from the CMV clinical isolate to confirm the fidelity of the PCR reaction.

Table 1 shows the variation detected in these isolates. The numbering used corresponds to the attached sequence listings.

The amino acid sequence for the amplified region was determined from the DNA sequence by means of the triplet codon designations.

TABLE 1

| Variant No | Sequence Changes | Coding Changes |
|---|---|---|
| 1 | 1991 T-A | 612 Leu-His |
|   | 2020 A-T | 622 Asn-Tyr |
| 2 | 1990 C-G | 612 Leu-Val |
|   | 2031 C-T | — |
|   | 2034 G-A | — |
|   | 2037 C-T | — |
| 3 | 2019 G-C | — |
| 4 | 2019 G-C | — |
| 5 | 1990 C-T | 612 Leu-Phe |
|   | 2031 C-T | — |
|   | 2034 G-A | — |
|   | 2037 C-T | — |
| 6 | 2019 G-C | — |
| 7 | 2019 G-C | — |
| Isolate No |  |  |
| 8 | 2019 G-C | — |
| 9 | 2019 G-C | — |
| 10 | 2019 G-C | — |
| 11 | 2019 G-C | — |
| 12 | 1977 T-C | — |
|   | 2019 G-C | — |
| 13 | 2090 A-G | 645 Asp-Gly |
| 14 | 2088 C-G | — |
|   | 2090 A-G | 645 Asp-Gly |

REFERENCE

Banks T., et al (1989). J. Gen. Virol. 70:979–985.
Chee M. S., et al (1989). Curr. Top. Imm. Microbiol. In Press.
Chen E. Y. and Seeburg P. H. (1985). DNA 4, 165–170.
Cranage M. P., et al (1986). EMBO J. 5:3057–63.
Cranage M. P., et al (1988). J. Virol. 62:1416–1422.
Gompels U. A., et al (1987). J. Gen. Virol. 68:793–803.
Liu N.-Y. C., et al (1989). Presentation at the 7th International Congress of Immunology, Berlin 1989, Abstract Number 98–59.
Rasmussen L. E., et al (1984). Proc. Natl. Acad. Sci. 79:616–620
Saiki R. K., et al (1988). Science 239,487–491
Sambrook J. Fritsch E. F. and Maniatis T. (1989) Molecular Cloning: A Laboratory Manual 2nd Edition, Coldspring Harbor Laboratory Press, Coldspring Harbor, N.Y.
Utz U., et al (1989). J. Virol. 63:1995–2001.

We claim:

1. A peptide having a sequence which is a variant of SEQ ID NO:2, said variant differing from SEQ ID NO:2 by one or more sequence variations, said sequence variations being substitutions selected from the group consisting of 612 Leu to His,
612 Leu to Val,
612 Leu to Phe,
622 Asn to Tyr, and
645 Asp to Gly.

2. A peptide having a sequence which is a variant of a portion of SEQ ID NO:2, said portion including at least one of amino acid residues 612, 622 and 645 of SEQ ID NO:2 and said variant differing from said portion of SEQ ID NO:2 by one or more sequence variations, said sequence variations being substitutions selected from the group consisting of 612 Leu to His,
612 Leu to Val,
612 Leu to Phe,
622 Asn to Tyr, and
645 Asp to Gly.

3. A peptide according to claim 2 wherein said portion consists of residues 609 to 629 of the HCMV gB protein.

4. A peptide according to claim 2 wherein said portion consists of residues 638 to 653 of the HCMV gB protein.

5. A fusion protein which comprises a peptide according to claim 1.

6. A fusion protein which comprises a peptide according to claim 2.

7. A fusion protein which comprises a peptide according to claim 3.

8. A fusion protein which comprises a peptide according to claim 4.

9. A pharmaceutical composition comprising a peptide according to claim 1 together with a pharmaceutically acceptable diluent or carrier therefor.

10. A pharmaceutical composition comprising a peptide according to claim 2 together with a pharmaceutically acceptable diluent or carrier therefor.

11. A pharmaceutical composition comprising a fusion protein according to claim 5 together with a pharmaceutically acceptable diluent or carrier therefor.

12. A pharmaceutical composition comprising a fusion protein according to claim 6 together with a pharmaceutically acceptable diluent or carrier therefor.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 366 base pairs
        ( B ) TYPE: nucleic acid
        ( C ) STRANDEDNESS: double
        ( D ) TOPOLOGY: unknown ( i i ) MOLECULE TYPE: DNA (genomic)

( i i i ) HYPOTHETICAL: NO ( i v ) ANTI-SENSE: NO ( v i ) ORIGINAL SOURCE:
        ( B ) STRAIN: AD169

( i x ) FEATURE:
        ( A ) NAME/KEY: CDS
        ( B ) LOCATION: 1..366

( x i ) SEQUENCE DESCRIPTION: SEQ ID NO:1:

```
AAG  GTG  CTG  CGT  GAT  ATG  AAC  GTG  AAG  GAA  TCG  CCA  GGA  CGC  TGC  TAC      48
Lys  Val  Leu  Arg  Asp  Met  Asn  Val  Lys  Glu  Ser  Pro  Gly  Arg  Cys  Tyr
 1                        5                        10                       15

TCA  CGA  CCC  GTG  GTC  ATC  TTT  AAT  TTC  GCC  AAC  AGC  TCG  TAC  GTG  CAG      96
Ser  Arg  Pro  Val  Val  Ile  Phe  Asn  Phe  Ala  Asn  Ser  Ser  Tyr  Val  Gln
                    20                       25                       30

TAC  GGT  CAA  CTG  GGC  GAG  GAC  AAC  GAA  ATC  CTG  TTG  GGC  AAC  CAC  CGC     144
Tyr  Gly  Gln  Leu  Gly  Glu  Asp  Asn  Glu  Ile  Leu  Leu  Gly  Asn  His  Arg
               35                        40                       45

ACT  GAG  GAA  TGT  CAG  CTT  CCC  AGC  CTC  AAG  ATC  TTC  ATC  GCC  GGG  AAC     192
Thr  Glu  Glu  Cys  Gln  Leu  Pro  Ser  Leu  Lys  Ile  Phe  Ile  Ala  Gly  Asn
          50                       55                       60

TCG  GCC  TAC  GAG  TAC  GTG  GAC  TAC  CTC  TTC  AAA  CGC  ATG  ATT  GAC  CTC     240
Ser  Ala  Tyr  Glu  Tyr  Val  Asp  Tyr  Leu  Phe  Lys  Arg  Met  Ile  Asp  Leu
 65                      70                       75                       80

AGC  AGT  ATC  TCC  ACC  GTC  GAC  AGC  ATG  ATC  GCC  CTG  GAT  ATC  GAC  CCG     288
Ser  Ser  Ile  Ser  Thr  Val  Asp  Ser  Met  Ile  Ala  Leu  Asp  Ile  Asp  Pro
                    85                       90                       95

CTG  GAA  AAC  ACC  GAC  TTC  AGG  GTA  CTG  GAA  CTT  TAC  TCG  CAG  AAA  GAG     336
Leu  Glu  Asn  Thr  Asp  Phe  Arg  Val  Leu  Glu  Leu  Tyr  Ser  Gln  Lys  Glu
               100                      105                      110

CTG  CGT  TCC  AGC  AAC  GTT  TTT  GAC  CTC  GAA                                   366
Leu  Arg  Ser  Ser  Asn  Val  Phe  Asp  Leu  Glu
          115                      120
```

( 2 ) INFORMATION FOR SEQ ID NO:2:

( i ) SEQUENCE CHARACTERISTICS:
            ( A ) LENGTH: 122 amino acids
            ( B ) TYPE: amino acid
            ( D ) TOPOLOGY: linear ( i i ) MOLECULE TYPE: protein ( x i ) SEQUENCE DESCRIPTION: SEQ ID NO:2:

| Lys | Val | Leu | Arg | Asp | Met | Asn | Val | Lys | Glu | Ser | Pro | Gly | Arg | Cys | Tyr |
|---|---|---|---|---|---|---|---|---|---|---|---|---|---|---|---|
| 1 | | | | 5 | | | | | 10 | | | | | 15 | |
| Ser | Arg | Pro | Val | Val | Ile | Phe | Asn | Phe | Ala | Asn | Ser | Ser | Tyr | Val | Gln |
| | | | 20 | | | | 25 | | | | | 30 | | | |
| Tyr | Gly | Gln | Leu | Gly | Glu | Asp | Asn | Glu | Ile | Leu | Leu | Gly | Asn | His | Arg |
| | | | 35 | | | | 40 | | | | | 45 | | | |
| Thr | Glu | Glu | Cys | Gln | Leu | Pro | Ser | Leu | Lys | Ile | Phe | Ile | Ala | Gly | Asn |
| | | 50 | | | | 55 | | | | | 60 | | | | |
| Ser | Ala | Tyr | Glu | Tyr | Val | Asp | Tyr | Leu | Phe | Lys | Arg | Met | Ile | Asp | Leu |
| 65 | | | | | 70 | | | | | 75 | | | | | 80 |
| Ser | Ser | Ile | Ser | Thr | Val | Asp | Ser | Met | Ile | Ala | Leu | Asp | Ile | Asp | Pro |
| | | | | 85 | | | | | 90 | | | | | 95 | |
| Leu | Glu | Asn | Thr | Asp | Phe | Arg | Val | Leu | Glu | Leu | Tyr | Ser | Gln | Lys | Glu |
| | | | 100 | | | | | 105 | | | | | 110 | | |
| Leu | Arg | Ser | Ser | Asn | Val | Phe | Asp | Leu | Glu | | | | | | |
| | | | 115 | | | | 120 | | | | | | | | |

( 2 ) INFORMATION FOR SEQ ID NO:3:

( i ) SEQUENCE CHARACTERISTICS:
            ( A ) LENGTH: 25 base pairs
            ( B ) TYPE: nucleic acid
            ( C ) STRANDEDNESS: single
            ( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
            ( B ) STRAIN:

( i x ) FEATURE:
            ( A ) NAME/KEY: CDS
            ( B ) LOCATION: 1..25

( x i ) SEQUENCE DESCRIPTION: SEQ ID NO:3:

GAGGACAACG AAATCCTGTT GGGCA                                                                25

( 2 ) INFORMATION FOR SEQ ID NO:4:

( i ) SEQUENCE CHARACTERISTICS:
            ( A ) LENGTH: 25 base pairs
            ( B ) TYPE: nucleic acid
            ( C ) STRANDEDNESS: single
            ( D ) TOPOLOGY: unknown ( i i ) MOLECULE TYPE: DNA ( i i i ) HYPOTHETICAL: NO ( i v ) ANTI-SENSE: NO ( v i ) ORIGINAL SOURCE:
            ( B ) STRAIN:

( i x ) FEATURE:
            ( A ) NAME/KEY: CDS (B) LOCATION: 1..366

(xi) SEQUENCE DESCRIPTION: SEQ ID NO:4:

GTCGACGGTG GAGATACTGC TGAGG 25